United States Patent [19]

Comfort et al.

[11] 3,938,386

[45] Feb. 17, 1976

[54] METHOD AND APPARATUS FOR MONITORING TEMPERATURES DURING CATALYTIC REGENERATION FROM A CONTINUOUSLY MOVING INFRARED SCANNING AND DETECTION UNIT FIXEDLY MOUNTED ABOARD AN AIRCRAFT

[75] Inventors: Armand C. Comfort, Belmont; Harold D. Messner, Fremont, both of Calif.

[73] Assignee: Chevron Research Company, San Francisco, Calif.

[22] Filed: Mar. 15, 1973

[21] Appl. No.: 341,649

[52] U.S. Cl. ............ 73/355 R; 23/230 A; 23/288 B; 73/340; 73/362.8; 250/334; 250/342; 252/416; 315/12 R
[51] Int. Cl.² .................. G01J 5/08; B01J 37/08; G01N 25/48
[58] Field of Search .......... 23/288 B, 288 H, 230 A; 73/340, 355 R, 355 EM, 362.8, 362.5, DIG. 7, 349; 250/334, 342; 252/416; 356/44; 236/15 B; 178/DIG. 8, DIG. 33; 315/12

[56] References Cited
UNITED STATES PATENTS

| | | | |
|---|---|---|---|
| 2,022,440 | 11/1935 | Slough | 73/362 R X |
| 2,437,173 | 3/1948 | Rutherford | 315/12 UX |
| 2,981,590 | 4/1961 | Parker | 252/416 |
| 3,153,147 | 8/1964 | Bradley et al. | 73/355 R X |
| 3,191,035 | 6/1965 | Brumfield et al. | 250/334 |
| 3,430,045 | 2/1969 | Bjork et al. | 73/355 R X |
| 3,752,914 | 8/1973 | England et al. | 178/DIG. 8 X |
| 3,752,915 | 8/1973 | Parker et al. | 178/DIG. 8 X |
| 3,821,895 | 7/1974 | Sumikawa et al. | 73/355 R X |

Primary Examiner—Richard C. Queisser
Assistant Examiner—Frederick Shoon
Attorney, Agent, or Firm—R. L. Freeland, Jr.; H. D. Messner

[57] ABSTRACT

Careful and accurate indication of regeneration temperatures of catalysts associated with the refining of hydrocarbons such as occurring in catalyst-aided hydrocracking and catalyst-aided reforming processes—in real time—occurs by monitoring—from an overflying aircraft—the infrared energy, say in a frequency range greater than $300 \times 10^9$ but not more than $10^{15}$ Hertz, emitted from a plurality of distributed metallic studs mounted as by welding to the exterior surface of the sidewall of a vessel undergoing catalytic regeneration. The dynamic temperature variation of such energy rays readily indicates regeneration temperatures of the catalyst interior of the vessel. The studs extend through the insulation of the vessel but do not penetrate its interior. Where the regeneration process is cyclically occurring, not only is there a marked decrease in the time required for regeneration, but there is also better statistical certainty that full regeneration of the catalyst has occurred. Further, by mounting the infrared scanning and detection unit aboard a continuously moving aircraft flying a constant elevational, circular path over the vessel, the temperature of catalyst interior of the vessel over the full 360-degree circumference of the vessel can be quickly and accurately determined.

Such scanning and detection unit preferably includes novel enhancement circuitry for restoring the infrared energy signals after detection, say under operating conditions concomitant with atmospheric degradation ("clutter") or image blur of the emitted infrared signals.

3 Claims, 7 Drawing Figures

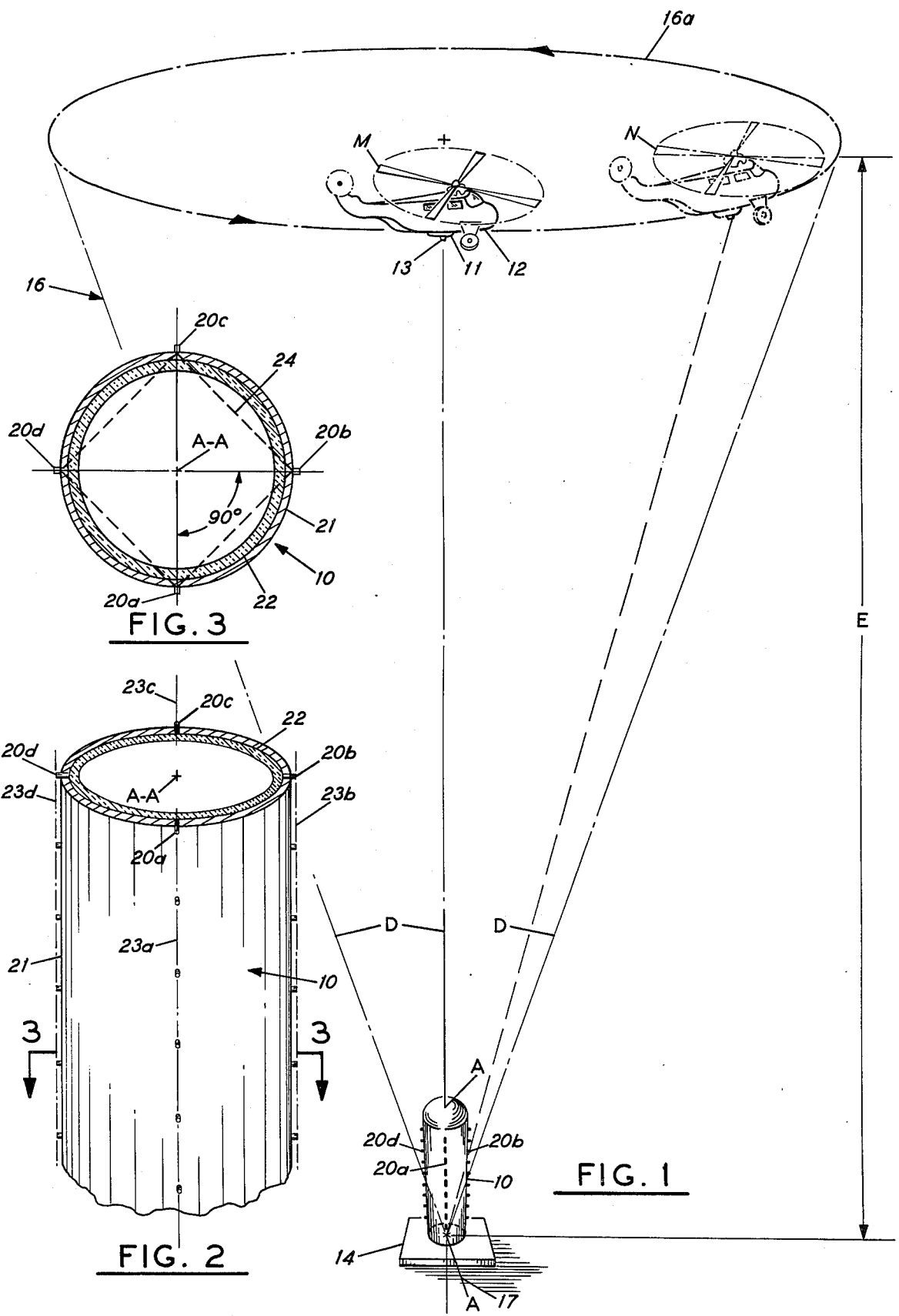

METHOD AND APPARATUS FOR MONITORING TEMPERATURES DURING CATALYTIC REGENERATION FROM A CONTINUOUSLY MOVING INFRARED SCANNING AND DETECTION UNIT FIXEDLY MOUNTED ABOARD AN AIRCRAFT

CROSS-REFERENCE TO RELATED APPLICATION

Reference should also be had to a copending application for "Method and Apparatus for Monitoring Temperatures During Catalytic Regeneration", Ser. No. 341,626, filed concurrently herewith on Mar. 15, 1973, in the names of D. Roger Loper and Water E. Fauerso and assigned to the assignee of the present application.

FIELD OF THE INVENTION

This invention relates to a method and apparatus for improving the efficiency of catalyst regeneration associated with the refining of hydrocarbons such as occurring in catalyst-aided hydrocracking and catalyst-aided reforming processes. More particularly, this invention relates to an infrared scanning method and apparatus for improving catalytic regeneration in such refining operations through careful monitoring of temperatures within vessels associated with regeneration process from an overflying aircraft.

SUMMARY OF THE INVENTION

In accordance with method aspects of the present invention, accurate incidation of regeneration temperatures of catalysts—in real time—instantaneously occurs by monitoring—from an overflying aircraft—the infrared energy, say in a frequency range greater than $300 \times 10^9$ but not more than $10^{15}$ Hertz, emitted from a plurality of distributed metallic studs mounted as by welding to the exterior surface of the sidewall of a vessel undergoing catalytic regeneration.

The dynamic temperature variation of such energy rays readily and quickly indicate regeneration temperatures of the catalyst interior of the vessel. The studs extend through the insulation of the vessel but do not penetrate its interior. Where the regeneration process is cyclically occurring, not only is there a marked decrease in the time required for regeneration, but there is also better statistical certainty that full regeneration of the catalyst has occurred.

In accordance with apparatus aspects of the present invention, real time presentation of the regeneration cycle are provided by an infrared scanning and detection unit mounted to a continuously moving aircraft flying a circular, constant elevational path over the vessel associated with the regeneration process. The scanning and detection unit includes a fixed position camera unit for detecting infrared energy emitted from studs welded to the vessel. As infrared radiation is emitted from the studs, the camera unit detects the energy by means of an infrared detector. The detector converts the infrared signal to direct video signals. The latter are divided and then processed in parallel circuits: (i) in a first circuit including an image enhancement circuit in series with a display unit aboard the aircraft and (ii) in a second circuit also in series with the display unit including a delay line matrix for synchronizing time and geometric characteristics of the two processed data streams. Within the enhancement circuit, item (i), supra, the video signals are enhanced based on whether the source of infrared emission was apparently stationary with respect to a fixed geographical location at say the earth's surface. In that way, only signals emitted from the studs are enhanced. The latter, after amplification, along with the direct ("raw") video signals are fed to twin cathode ray tubes within the display unit where side-by-side displays can be photographed by a recording camera attached to the cathode ray tubes. The sweep of the cathode ray tubes is matched to that of the camera so that the resulting images are readily structured to yield both temperature and locational information related to the regeneration process. Also, by adjusting the temperature sensitivity of the infrared camera unit, wave front catalyst temperature differences can be indicated over a rather wide range of operating temperatures, say from 1° to 1360°F.

BACKGROUND OF THE INVENTION

Catalytic processes play a heavy role in refining carbonaceous materials. Likewise, regeneration of the involved catalyst logically occupies a correspondingly large amount of a process engineer's time and efforts. For example, in the conversion of high-boiling non-gasoline hydrocarbons into lower boiling gasoline components, the catalytic-aided process steps of treating, decomposition, fractionating, gasoline stabilization, and absorption polymerization requires, for the most part, cyclic or occasional regeneration of the involved catalysts, see, for example, Kirk-Othmer, *Encyclopedia of Chemical Technology*, 2nd Edition, Volume 15, "Petroleum (Refinery Processes)", page 15 et seq.

Catalysts are usually classified by function—fixed bed, movable bed, or fluid bed—and by process condition, three typical process examples being set forth below to better illustrate the practice of catalyst-aided processes in general and the regeneration of involved catalyst in particular.

1. Early catalytic crackers were usually of the fixed bed type but today most cracking is carried out in moving or fluid beds. Regeneration temperatures and pressures in moving and fluid beds are usually in the ranges of 1,000°–1,210°F and 8 to 30 psig, respectively, 2. Modern hydrocrackers employed in hydrocracking (an efficient low-temperature catalytic method for converting refractory middle-boiling or residue streams to high-octane gasoline or jet fuel, etc.) use fixed bed processing for the most part. After hydrogen has been mixed with the feed, the mixture is heated and contracted with a catalyst in a separate fixed-bed reactor at specified hydrogen partial pressures. Regeneration pressure and temperature of the catalyst are usually within the ranges of 400° to 800°F and 10 to 2,000 psig, respectively, and 3. Modern catalytic reformers associated with catalytic reforming (upgrading naphthas into high-grade components for fuel blending or petroleum usage in which molecules are rearranged to give a higher anti-knock quality at the expense of yield) also employ fixed beds in the main, e.g., less than 5% of the U.S. reforming capacity, it is estimated, utilizes fluid or moving bed processes. Temperature and pressures for regeneration of catalyst involved in reforming are in the ranges of 800° to 1,500°F and 200 to 400 psig, respectively.

In controlling regeneration temperature and pressure conditions within the above processes, it has been found that the aforementioned variables are usually not monitorable in a direct fashion. Safe engineering practice dictate against the use of internal sensors, for the most part, because associated control and energization elements must, in some manner, penetrate the sidewalls of the vessels undergoing regeneration. Instead, temperatures and pressures of associated regeneration fluids flowing relative to the vessel are monitored. Temperatures of the catalytic regeneration process are then inferred from temperature and pressure values measured at external sensing locations.

Although infrared scanning techniques have been used in many refinery applications, such applications of which we are aware, have been limited in scope and function. Moreover, such techniques were thought not to have the capability of monitoring regeneration processes to which the present invention is directed since such vessels are for the most part heavily clad with insulation. Thus, metallic sidewalls (which could be associated with interim regeneration temperature characteristics) are almost totally hidden from camera view, especially if such camera units are remotely located within an aircraft overflying the vessel undergoing regeneration under conditions that are conductive to atmospheric degradation ("clutter") and image blur of the emitted infrared energy.

OBJECT OF THE INVENTION

An object of the present invention is the provision of the novel method and apparatus for improving efficiency of regeneration of catalysts employed in catalytic processes in general and catalytic-hydrocracking and -reforming processes in particular through the careful infrared monitoring of temperatures associated with catalytic regeneration within reactors or within separate regeneration facilities of vessels associated with the regeneration process from an overflying aircraft.

Further objects and features of the present invention will become more apparent to those skilled in the art in the following detailed description of preferred embodiments, wherein, FIG. 1 is a perspective view of a vessel undergoing catalytic regeneration, such vessel being monitored by means of an infrared scanning and detection unit fixedly mounted aboard a continuously moving aircraft flying a circular course about the vessel, such unit detecting infrared energy emitted from a plurality of metallic studs mounted to the sidewall of the vessel extending through the insulation thereof;

FIG. 2 is a detail drawing of the vessel of FIG. 1 illustrating the orientation of the metallic studs with respect to the continuously moving aircraft;

FIG. 3 is a section taken along line 3—3 of FIG. 2;

DETAILED DESCRIPTION OF THE INVENTION

Figures 4, 5:
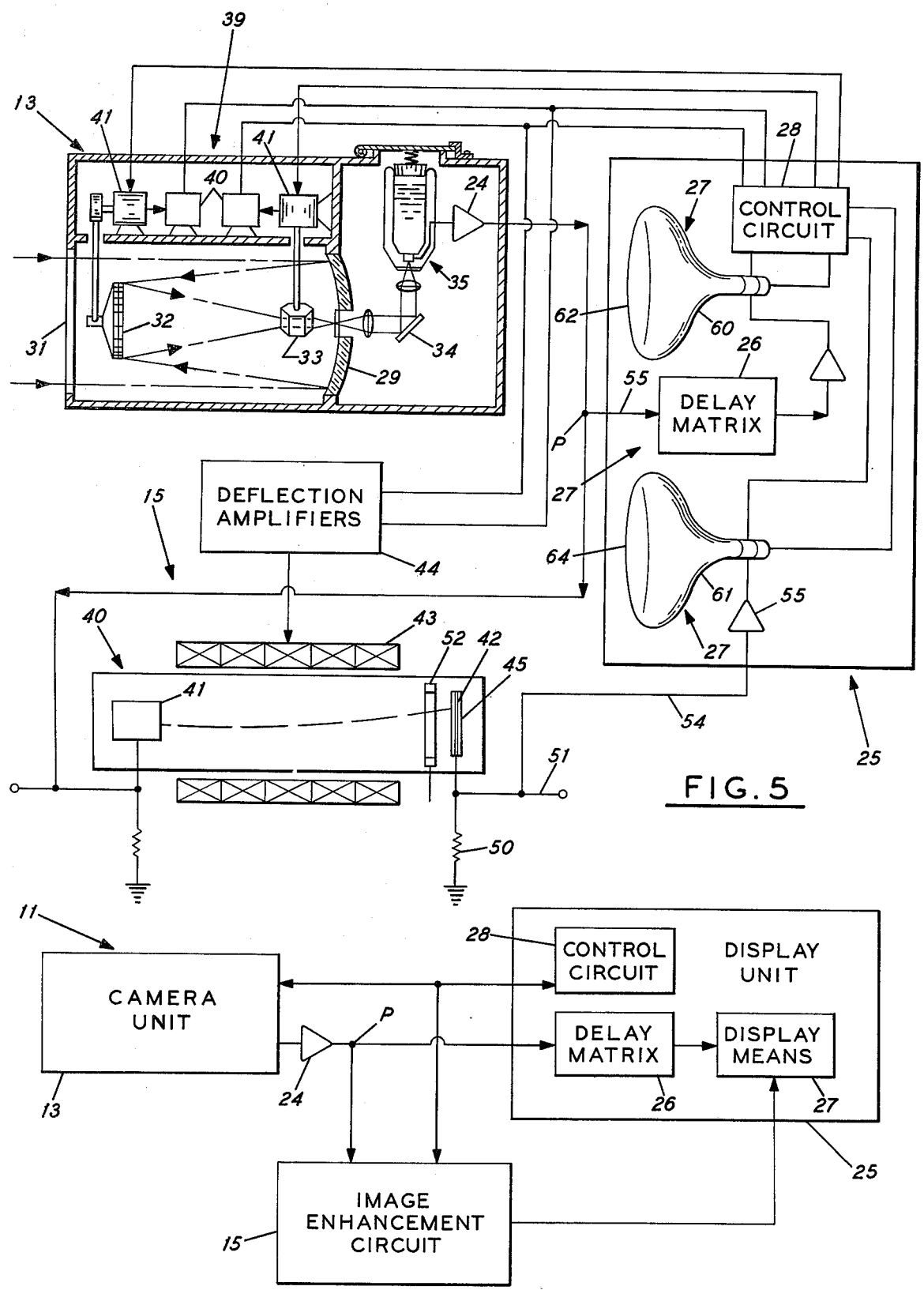
FIG. 4 is a block diagram of the infrared scanning and detection unit of FIG. 1.
FIG. 5 is a more detailed circuit diagram, partially schematic, of the infrared scanning and detection unit of FIG. 4.

Referring now to FIG. 1, temperatures interior of vessel 10 undergoing catalytic regeneration are quickly and easily indicated by infrared scanning and detection unit 11 fixedly mounted aboard continuously moving aircraft 12, such as a helicopter. Vessel 10 is associated with the refining of hydrocarbons in general and in hydrocracking and reforming processes in particular. Since the temperatures interior of the vessel 10 are indicative of the catalytic regeneration process and such temperatures dynamically vary the function of catalytic position within the vessel, the scanning and detection unit 11 must be able to dynamically detect slight temperature variations from position-to-position along the vertical extent of the vessel 10.

In accordance with the present invention, scanning and detection unit 11 provides the required temperature resolution in the vertical plane of the vessel 10 in a highly efficient manner from its fixed position aboard the aircraft 12. As indicated, the scanning and detection unit 11 includes a camera unit 13 fixedly positioned adjacent to an aperture through which the camera unit 13 projects. The flight pattern of the aircraft 12 is carefully controlled so that the camera unit 13 remains focused upon the vessel 10 during the entire scanning operation. That is to say, the aircraft 12 is not permitted to deviate from a fixed elevational, circular heading above the vessel 10 during the scanning operation. Reasons for the aforementioned flight pattern will appear below. Suffice it to say, after infrared energy emitted by the vessel under survey is detected and converted to video signals by camera unit 13, the resulting video signals are further processed within an image enhancement circuit also located aboard the aircraft for restoration purposes should signal degradation be occurring say due to geographical or atmospheric conditions attendant to the scanning operation.

Algorithm of the enhancement process is as follows: enhancement of signals occurs only if the sources of infrared energy are stationary with respect to a fixed geographical location at the earth's surface about which the aircraft 12 is undergoing circular movement. Accordingly, the position of the aircraft 12 must be carefully maintained in a preselected series of equi-height scanning stations with respect to the aforementioned geographical location.

In this regard, note the morphology of motion of the aircraft 12 is defined to be along an inverted base 16a of a right-circular, imaginery cone 16. The flight cone 16 is also seen to have a vertex 17 coincident with (i) the fixed, horizontal foundation 14 of vessel 10 and (ii) the vertical axis of symmetry A—A of the vessel 10; the cone 16 is also seen to have an altitude equal to the elevation E of the aircraft 12. Accordingly, the slant of the cone 16 is equivalent to the range distance D separating the aircraft 12 from foundation 14 of the vessel 11, i.e., from the earth's surface at any instant of time during the scanning operation. Of course, the geographic coordinates of the scanning stations along the cone 16 are known since the intersection of the vertex 17 with axis A—A of the vessel 10 is at a known geographic position at the earth's surface.

In operation, the camera unit 13 produces a series of images of the vessel 10 as the aircraft 12 traces its heading along base 16a of flight cone 16, the aircraft 12 maintaining a fixed elevation E above the earth's surface during the scanning operation. The vertical extent of camera image and hence available vessel scanning region, is, of course, variable so as to allow the infrared camera unit 13 to scan the entire vessel, say when the vessel 10 is used as a separate regeneration facility in a fluid-bed or moving-bed regeneration process, or scan only a section of the vessel 10, say when the vessel is associated with a fixed-bed process.

The principle of operation of the camera unit 13 is relatively simple. Hot objects give off higher frequencies than do cooler objects. It follows that accurate monitoring of infrared energy in a frequency range say greater than $300 \times 10^9$ but less than $10^{15}$ Hertz can provide meaningful indications of catalytic regeneration temperatures, provided the temperature indicated by the camera unit 13 is representative of the true catalyst temperatures. A further complication to the monitoring operation resides in the fact that the aircraft can be subject to atmospheric conditions conducive to degradation of the emitted signals before their detection by camera unit 13.

In accordance with the present invention, indication of true temperature conditions interior of the vessel 10 of FIG. 2 is inferred from a series of four sets of studs 20a, 20b, 20c and 20d, attached as by welding to the exterior of sidewall 21 of the vessel 10. Each set protrudes through insulation 22 so that unattached ends are visible as shown in FIG. 1 but do not pierce the interior of the sidewall 21. Studs of each set 20a, 20b, 20c or 20d are visible from aircraft 12 as a function of several factors including slant distance D between camera unit 13 and the vessel 10 as well as the instanteous field of view of camera unit 13 relative to the positions of the stud sets 20a, 20b, 20c and 20d. With regard to the latter, it should be noted that when the aircraft 12 intersects a common vertical plane through a set of studs 20a, 20b, 20c or 20d and axis A—A of the vessel 10, say at position M in FIG. 1, only the intersected set (in this case, set 20a) will be viewable by the camera unit 13. Between the aforementioned common vertical planes of the sets 20a, 20b, 20c, and 20d, say at position N 45 degrees between vertical planes through stud sets 20a and 20d, however, the two aforementioned sets are both simultaneously viewable by the camera unit 13.

Orientation of the studs is carefully controlled in the aforementioned preselected manner, i.e., along four vertical columns coextensive with insulation 22 of FIG. 2 but having a "visible" edge intersecting the unattached ends of each stud set 20a, 20b, 20c, or 20d along four vertical lines 23a, 23b, 23c and 23d. It is also apparent from FIG. 3 that each set 20a, 20b, 20c and 20d defines a series of exterior locations coincident with a common vertical plane passing through both the unattached stud ends of each set and intersect at axis of symmetry A—A of vessel 10. At axis A—A of the vessel, the angle of intersection between adjacent common planes is, of course, 90°.

In the horizontal direction, but perpendicular to axis A—A, orientation is likewise carefully controlled. In more detail, as seen best in FIG. 3, individual studs of the sets 20a, 20b, 20c, and 20d are horizontally aligned to form corners of a series (or family) of imaginary squares 24 horizontally stacked in imaginary tiers. Each such tier is symmetrical about axis A—A of the vessel 10 and vertically displaced by the constant spacing between individual studs comprising each set 20a, 20b, 20c and 20d.

Associated with the aforementioned series of exterior locations are sets of imaginary, equi-spaced temperature stations interior of the vessel 10, not shown. Each such set of imaginary stations of each column also lies in the aforementioned vertical plane and each intersects that plane along a vertical line that is tangent to the interior surface of the sidewall 21. The interior stations of each set are also laterally offset from corresponding exterior locations by a distance equal to at least the thickness of the sidewall 21 and the thickness of the insulation 22. In addition, if the length of each stud is above the exterior surface of insulation 22, such incremental length must also be added to obtain the aforementioned lateral offset distance. But, if the stud height is coincidental with the outer surface of the insulation 22, it is apparent that the previously mentioned plane of reference of each column will intersect the unattached stud ends along vertical lines that also would be tangent to the outer surface of insulation 22.

Stud patterns other than the aforementioned discontinuous column arrangement of FIG. 1, could also be used. For example, the studs can be oriented in four sets of vertically extending, cyclically repeating five-spot patterns. Each center spot of each set of 5-spot patterns would be vertically aligned along a common line. Furthermore, adjacent lines or columns would be separated by an arcuate distance equal to one-fourth of the total circumference of vessel 10. Each 5-spot pattern would likewise be positioned on an imaginary section intersecting the outer unattached surfaces of the studs and having an axis of formation coincident with the axis of symmetry A—A of the vessel 10.

As a still further modification of the stud pattern of FIG. 2, it is also contemplated that the stud sets 20a, 20b, 20c and 20d could also be oriented in four sets of sinusoidal patterns, each having a vertical line as a principal reference axis tangent with the outer surface of insulation 22. Note that in each of the aforementioned sinusoidal patterns, the unattached ends of the studs would be positioned in imaginary curve section having an axis of formation also coincident with the axis to the symmetry A—A of vessel 10.

It should be apparent that in all of the aforementioned stud patterns, individual studs of each set 20a, 20b, 20c and 20d must be horizontally aligned with at least two additional studs to form a morphology of two-dimensional figures stackable in tiers symmetrical about axis A—A of the vessel 10. With respect to the embodiment depicted in FIG. 2, as well as to the sinusoidal stud orientation described above, such figures can comprise a family of squares symmetrical about the axis A—A of the vessel 10. With respect to the five-spot stud patterns, the morphology becomes more complexed, changing from a square to an octagon figure in successively located tiers.

Process of mounting the sets of studs to the vessel 10 is straightforward: after each stud has been correctly positioned in any of the aforementioned patterns, welding of the studs are carried out using conventional welding techniques. The vessel 10 can then be stress-relieved.

FIG. 4 illustrates the operational aspects of the scanning and detection unit 11 of the present invention.

As indicated, the scanning and detection unit 11 is seen to include—in addition to camera unit 13—an image enhancement 15 and a display unit 25 comprising a delay matrix 26 and cathode ray display means 27. Briefly, in operation, the camera unit 13 scans the vessel, the emitted infrared energy is converted to direct video signals. The latter are first amplified by amplifier 24 then divided at junction point P and finally processed as two separate data streams: (i) a first stream is passed directly to cathode ray display means 27 through delay matrix 26; while (ii) a second stream is passed also to the display unit 25 but by way of image enhancement circuit 15. Within the display unit 25, each data stream is displayed side-by-side at cathode ray means 27 indicating the temperatures of the studs attached to the sidewall of the vessel undergoing regeneration. Control of the enhancement operation as well as synchronization of the sweeps of the camera unit 13, the image enhancement circuit 15 and display unit 25, is provided by control circuit 28. In this regard the horizontal and vertical sweeps of the camera unit 13 is synchronized by producing a series of positional signals in the manner explained below.

FIG. 5 illustrates the operation of camera unit 13, image enhancement circuit 15 and display unit 25 in detail.

As indicated, the infrared camera unit 13 includes a focusing spherical mirror 29 centrally disposed within a housing fixedly attached to a fixed support of the aircraft, not shown. Infrared radiation enters through optic window 31 and is focused by the mirror 29. The camera scans the total viewable space in two ways: vertically with oscillating mirror 32 and horizontally with multi-sided prism 33. The resulting scan radiation then propagates through lens system 34 to infrared detector 35. Infrared detector 35 converts the radiation signals to electrical video signals using a photovoltaic effect as provided by say a indium antimonide photovoltaic detector. Liquid nitrogen provides required cooling of the detector 35.

The principle of operation of the camera unit 13 is relatively simple. Hot objects give off higher frequencies of infrared rays than do other objects. In detecting the rays within an infrared frequency range greater than $300 \times 10^9$, but not more than $10^{15}$ Hertz, primary optics window 31 and spherical mirror 29 of the camera unit 13 form an image of the object at the prism 33. With regard to horizontal resolution of the object, assume prism 33 is an eight-sided prism and is rotating at about 200 revolutions per second. Accordingly, it follows that 1600 horizontal lines of identifying information could be scanned each second of operation of the camera unit 13. Likewise, if each scan frame at enhancement circuit 15 and display unit 25 contains 100 vertical lines, then 16 fraames of information are produced each second of camera operation. With regard to temperature resolution, such values are usually determined by comparing a object's infrared radiation to that of its surroundings background radiation or to that of a reference source expressed in the following equation $$P = \epsilon \sigma T^4 / \pi \quad (1)$$

where:
T is the absolute temperature in degrees Kelvin,
$\epsilon$ is the emissivity of the surface of the plane, and
$\sigma$ is the Stefan-Boltzmann constant of $5.6697 \times 10^{-8}$ watts/M$^2$K$^{-4}$ The video signal derived from a scene based on the difference in power being radiated from different areas of the scene may be expressed by taking the partial derivative of equation (1) above with respect to temperature, T, and emissivity $\epsilon$.

$$\Delta P_T = \frac{4\epsilon\sigma T^3}{\pi}\Delta T + \frac{\sigma T^4}{\pi} \quad (2)$$

Emissivity of a target may be considered to be a constant equal to unity with equation (2) becoming $$\Delta P = \frac{4\sigma T^3}{\pi}\Delta T \quad (3)$$

with $\Delta T = (T_2 - T_1)$ in which the power change ($\Delta P$) from one object has an emissivity of unity ($\epsilon = 1$) and a temperature $T_1$ as compared to that of a second object with an emissivity of 1 ($\epsilon = 1$) and a temperature of $R_2$.

Of course, the ratio of horizontal and vertical scanning frequencies of camera unit 13 can be altered if desired. In that way, the line raster can move slowly in a vertical direction. Thus, a photograph of the images at cathode ray display means 27 taken with an exposure time of 0.5 seconds or longer, can have superimposed upon itself at least two frames of interest so that line pattern of the moving image on the screen, is not noticeable. The resulting multi-frame photograph is referred to as a histogram while a single frame photograph is a thermogram. It should be apparent that the number of superimposed frames per histogram can be varied. By increasing the number per each scanning station, for example, a degree of noise immunity may also be achieved. In this regard, it should be noted that sophisticated statistical techniques may also be used in determining the aforementioned threshold number.

Timing synchronization between control circuit 28, camera unit 13, display unit 25 and enhancing circuit 15, can be critical. Not only must control circuit 28 provide for control of the contrast in brightness at the cathode ray display means 27 of the display unit 25 (contrast being a variable as the function of temperature range; brightness being variable as a function of temperature levels), but it also must coordinatee the sweeps of the aforementioned circuitry. That is to say, the sweeps of the camera unit 13 must be coordinated with those of enhancing circuit 15 and the cathode ray means 27. In this regard, positional signals for synchronizing the aforementioned sweeps are generated by camera unit 13 to a synchronizing unit 39, including a transducer mechanically attached to both mirror 32 and prism 33. That is to say, the positional signals are generated by photocell unit 40, linked to the drive means 41 of the mirror 32 and prism 33. Moreover, such signals can be directly related to known geographic coordinates associated with the individual vessel under survey since the aircraft's position relative to the vessel's axis of symmetry is readily determinable. In that way, final video information at cathode ray display means 27 can be coordinated in time and geometric similitude with camera unit 13.

After amplification by amplifier 24, the video signals are divided at junction point P and then processed in parallel circuits: (i) in a first circuit including the image enhancement circuit 15 and (ii) in a second circuit in series with the display unit 25.

With regard to the latter, circuit operation may require delaying the direct ("raw") data stream prior to its entry into the cathode ray display means 27. In accordance with the present invention, the required delay of the direct data stream can be provided by operation of conventional delay matrix 26. However, the duration of the delay should be carefully controlled, being at least equal to the repetition rate of the scanning sequence, i.e., equal at least to the scan interval of the scanning operation.

With regard to the former, enhancement circuit 15 is seen to include a storage tube 40 having an electron gun assembly 41. The gun assembly 41 produces a beam of electrons which travels towards and intersects target electrode 42 at the remote end of the storage tube. Along the storage tube surrounding the beam of travel are a series of deflection coils 43 whose magnetic fields are controlled by actuation of deflection amplifiers 44.

In operation, after emission from the gun assembly 41, the beam of electrons is directed along a series of lines in synchronism with the sweep of the camera unit 13. Such synchronization of signals are generated by camera unit 13 in cooperation with control circuit 28 as previously explained. The beam of electrons is incrementally deflected along a series of lines as a result of the magnetic fields generated by coils 43 in cooperation with activation of amplifiers 44. In this regard, the deflection coils 43 can be standard vidicon deflection coils matched to the storage tube 40 and amplifiers 44. The previously mentioned synchronization signals also deflect similar electron beams of cathode ray display means 27 within a display unit 25, such beams being deflected in time in geometric similitude to form similar raster patterns with that generated by camera unit 13.

The target electrode 42 of the storage tube 40 is also seen to include a panel 45 adjacent thereto formed of electrically conducting material such as nickel. A coating of dielectric material is added to panel 45 on a side in which the beam of electrons of the storage tube 40 fall. Such coating is characterized by its having a secondary emission less than unity and a high capacitance and resistance to provide a static decay rate or RC time constant sufficient to hold the electron's charge slightly longer than the time between scan intervals of the camera unit 13. A coating material having these characteristics is a first layer of highly resistant semiconductor material such as selenium (a T-type conductor, and a layer of cadmium selenide (an N-type conductor) wherein the interface between layers forms a rectifying barrier. The layer of cadmium selenide is bonded to the panel 45 using a conventional patching material compound.

Although the exact operational theory of the storage tube 40 is not exactly known, the target electrode 42 can be likened to an array of a large number of theoretical capacitors connected in parallel with a resistor. In operation, as the electron beam scans across theoretical capacitors when a video signal is present, a current flows so as to produce electrical signals at load resistor 50 and, at the same time, charging the theoretical capacitor. As the beam moves along in its raster scan, a charge is left on a theoretical path while leaving a theoretical capacitor open-circuited. The next time the search pattern scans this same raster line, the electron beam again crosses this theoretical capacitor. If the electron beam is modulated by a video signal from a target that has moved during the scan-interval relative to actual movement of the aircraft, the beam cannot deposit any additional electron charge under theoretical capacitor because of the equal electron charge left there by the previous scan. As a result, no current flows into theoretical RC charging circuit. This operation is repeated on all frequent-scan rasters so that the video signals forming moving infrared targets are canceled. In the case of a stationary target, however, which is provided by the studs attached to the vessel undergoing regeneration, however, the video signal modulated electron beam will either change in intensity and/or fall on a different area of target electrode 42. This change in the modulated beam results in electron charge being increased or deposited on a different theoretical capacitor to cause a current to flow through the load resistor 50 whereby an output signal is generated on the output line 51. As is conventional, a collector 52 is mounted in front of the target face to control any secondary electron emission therefrom. From storage tube 40, the enhanced signals pass to display unit 25 via conductor 54 and amplifier 56.

Cathode ray display means 27 of the display unit 25 of FIG. 5 includes not one cathode ray tube, but twin cathode ray tubes 60 and 61. As indicated, the cathode ray tube 60 and 61 provide for the display of the two streams of video information; that is, cathode ray 60 provides for the display of direct video signals at screen 62 from amplifier 24 via conductor 55, while cathode ray tube 61 displays enhanced signals at screen 64, generated by enhancement circuit 15 and entering thereto via conductor 54. It should be apparent that both screen 62 and 64 can be aligned in a side-be-side position alignment so that a single recording camera can be used to record the flickering images due to the emission of radiation energy from the studs attached to the vessel undergoing regeneration. As previously mentioned, the ratio of horizontal and vertical scanning frequencies of the display unit 25 can be altered to provide raster movement in a vertical direction. Thus, multiframe displays can be generated by the display unit 25, i.e., displayed at either one or both cathode ray tubes 60 and 61. Furthermore, the intensity of the images of the direct video signals at screen 62 of the cathode ray tube 60 can be compared, visually, with images of the enhanced video signals at screen 64 of the cathode ray tube 61. In that way, there can be provided a convenient basis to predict the temperatures interior of the monitored vessel even though the direct video signals may have undergone atmospheric degradation prior to detection of the camera unit 13 within the aircraft circling the vessel undergoing regeneration.

With regard to the use of camera unit 13 to measure the temperatures interior of the vessel, it should be recalled that the heat transfer characteristics of each catalyst bed within the vessel vary rapidly with time and location. Hence, the ability of the aircraft to circle the aforementioned vessel in a circular pattern assures that the information detected by the camera unit has been most representative of the true conditions interior of the vessel. The frequency scan of the camera unit can vary also, but should be high enough to provide for temperature indications as a function of time throughout each regeneration cycle of the vessel. In this regard, it has been found that photographs of the screens 62 and 64 of the cathode ray tube 60 and 61, respectively, can be generated accurately enough to provide the required information to control the regeneration process, if camera unit 13 is provided with the aforementioned horizontal and vertical scanning characteristics. In this regard, it should be noted that personnel within the aircraft are usually in direct radio contact with refinery personnel. Accordingly, as temperatures of the regeneration process are determined such temperature information can be quickly relayed to the refinery to control the regeneration process, as needed.

Figure 6A:
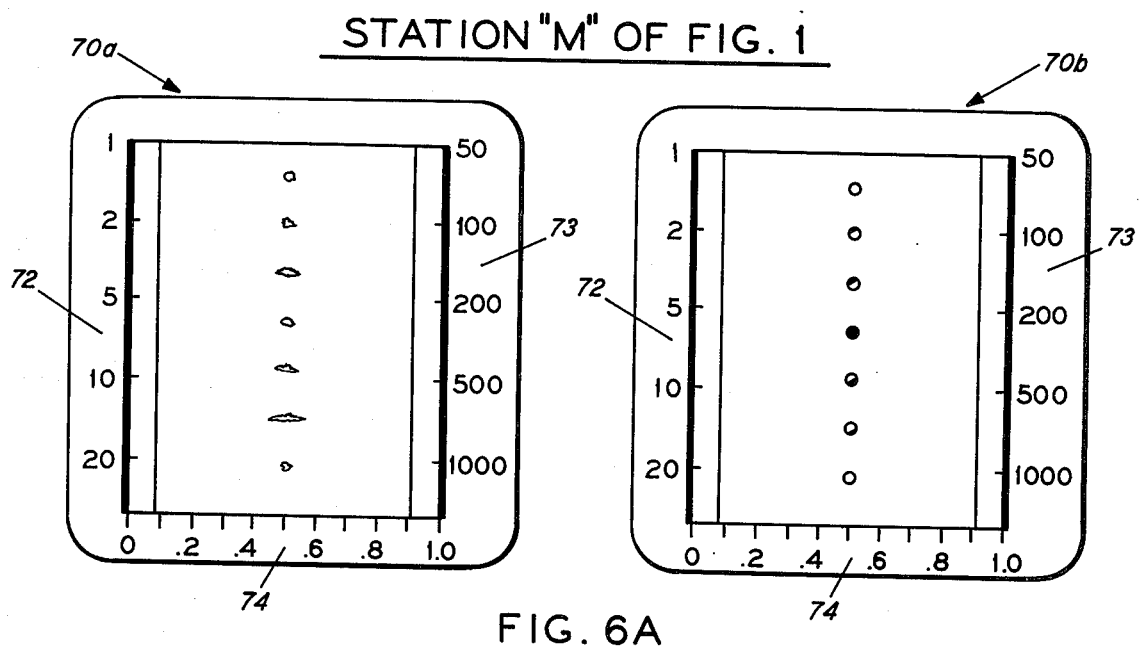
FIGS. 6a and 6b are photographs produced by the infrared scanning and detection unit of FIG. 5 in which temperatures associated with the plurality of studs of FIG. 1 in both direct and enhanced states are indicated and recorded on film.
Figure 6B:
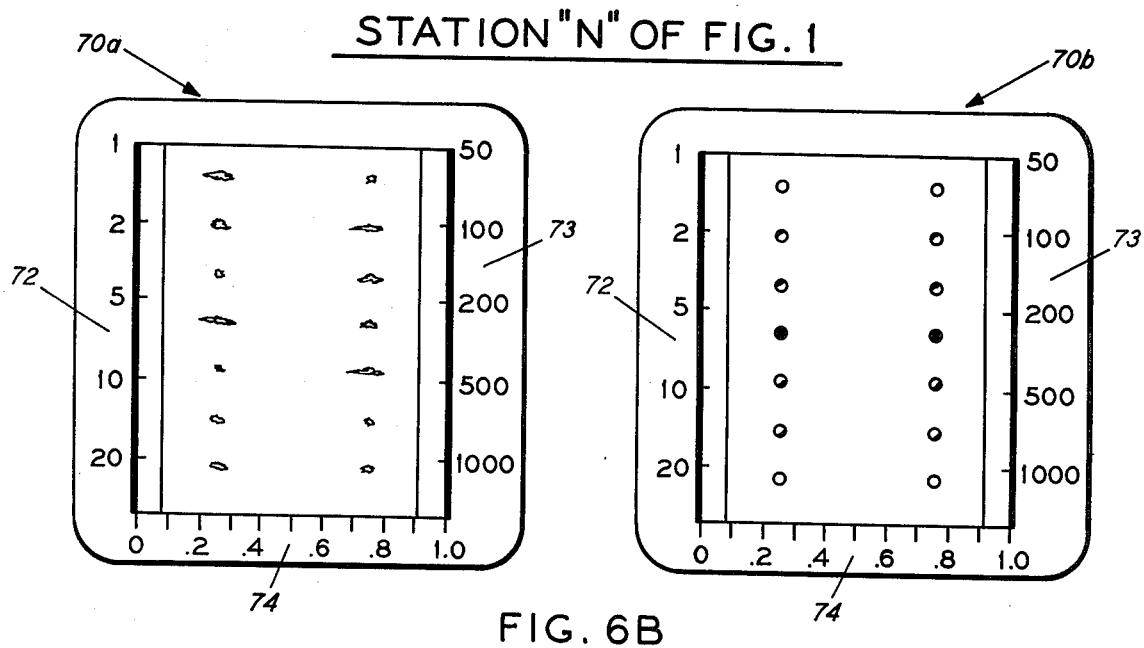

FIGS. 6a and 6b illustrate typical presentations of flickering images at the screens 62 and 64 of the cathode ray tube 60 and 61, respectively. As previously indicated with reference to FIG. 1, the camera unit 13 aboard the aircraft scans the vessel from a plurality of moving positions at a constant altitude, to particular position being noted, being indicated at angular scanning stations M and N on flight cone 16 of FIG. 1. Assume that the speed of the aircraft is known and the scanning rate has been adjusted so that positions of the stations M and N are coincident with adjacent scanning cycles of the scanning operation. Temperature differences between the real time images of the studs attached to the vessel undergoing regeneration at the flight stations M and N appear as black and white images at the cathode ray tubes 60 and 61 which change depending on the field of view of the camera unit. These images appear as flickering lines on the screens 62 and 64 of the cathode ray tube 60 and 61 respectively and can be photographed to produce separate first and second displays 70a to the left as viewed in FIGS. 6a and 6b and displays 70b viewed at the right in FIGS. 6a and 6b.

The quality of the displays 70a and 70b can vary markedly. As indicated, the displays 70a represent direct signal data generated by the camera unit 13 and displayed by the cathode ray tube 60. Each such display is associated with direct ("raw") data detected at stations M and N, respectively. Such images can be degraded such that the portions of the images representative of the studs of the monitored vessel can be distorted or completely canceled. On the other hand, the displays 70b of the FIGS. 6a and 6b relate to relative flight positions M and N of FIG. 1 and reflect enhanced images produced by the enhancement circuit 15 of the present invention. In order to sychronize operations, the enhanced display 70b of FIG. 6a is associated with station M and has been generated using data received at station M as well as data obtained in a prior scanning cycle, while the enhanced display 70b of FIG. 6b is associated with station N and has been generated using data obtained at both stations M and N. As noted, the displays 70b provides improved images indicative of the temperature of the studs attached to the vessel undergoing regeneration since both vertical and horizontnal resolution has been sharply improved by the processing in accordance with the method and apparatus of the present invention.

Sensitivity of the resulting display 70a and 70b can be indicated by the scale 72 and 73 placed on the left and right sides thereof as viewed (gradation: 1-1000). A gray scale 74 is presented at the bottom of the displays and represents a scale in which a shade of gray equals $\sqrt{2}$ times the intensity of the next preceding level. Not only are visual methods available to determine temperature levels of each display 70a and 70b, but also automatic machine comparisons can be used if desired. For example, a digital comparison circuit (not shown), say located internally of control circuit 28, could be used to automatically analyze the display 70a and 70b without need of human intervention, such circuit using a binary scale (1 and 0) in which the 1 state is a black dot and the 0 state is a white dot after analog-to-digital conversion of the video signals from the camera unit 13 has occurred. Each 1 or 0 state can be determined over a selected range of temperature shades between 0 and 1 states reflecting gradations of temperature levels within the selected range. Also, resulting displays can be compared—line-by-line—with previously obtained displays which represent instances in the regeneration cycle in which exceptional responsive levels occur. In that way, optimization of the currently recurring regeneration process can be obtained.

Although certain embodiments of the present invention have been illustrated and described, the invention is not meant to be limited by these embodiments, but the scope of the following claims. For example, it should be apparent to those skilled in the art that other image-enhancement techniques could be used in the method and apparatus of the present invention. In this regard, image-enhancement techniques utilizing the digital computer may be quite useful in combination with the method and apparatus of be quite useful in combination with the method and apparatus of this invention, such teachings being set forth in detail in the book "Computer Techniques and Image Processing", Harry C. Andrews, Academic Press (1970).

1. In the regeneration of a catalyst located interior of an insulation-clad vessel having an axis of symmetry, by elevating the temperature of said catalyst only after production of hydrocarbon products such as petrochemicals, gasolines, light-fuel oils and the like, has been terminated, the method of monitoring the efficiency of such regeneration process comprising the steps of:

i. prior to operation of said vessel and either production or regeneration processing modes, affixing a plurality of metallic stud members to the metallic sidewall of said vessel, said plurality of metallic stud members extending through said insulation of the vessel, and being associated with a set of imaginary laterally offset spatial positions interior of said vessel for identifying full top-to-bottom interior temperature readings within each catalyst bed when said vessel undergoes regeneration, ii. during regeneration of said catalyst, monitoring from an aircraft having known geographical coordinates with respect to said vessel at the earth's surface, infrared energy—in real time—being emitted from said plurality of metallic stud members defining a viewable space of said stud members in a frequency range greater than $300 \times 10^9$ but less than $10^{15}$ Hertz, iii. converting said detected infrared energy to electrical signals, iv. enhancing those portions of said electrical signals based on whether the detected energy represented thereby radiated from all sources including that from said stud members remains stationary during two adjacent scanning cycles as said aircraft overflies said vessel, v. dynamically indicating temperatures of said catalyst interior of said vessel for the purpose of optimizing said regeneration process by displaying said enhanced signals as a function of geometric and time variables associated with said stud members as viewed from said aircraft, and vi. cyclically repeating the scanning sequence as said aircraft overflies said vessel on a flight pattern of sufficient height so that, between said scanning cycles, said stud members appear to be stationary with respect to said aircraft.

2. Process of claim 1 in which said enhancing step (iii) is further characterized by the substeps of (a) modulating an electron beam of a storage tube as a function of geometric and time variables associated with a known set of geographical coordinates as said infrared energy is detected, said modulated electron beam of said storage tube providing enhanceable video information at an output means thereof, (b) storing said enhanceable video information for at least a subsequent scan interval of said storage tube and (c) developing enhanced signals for display from said stored video information corresponding to radition variations dependent upon whether said stud members emitting said infrared energy remain stationary as said aircraft overflies said vessel.

3. Process of claim 2 further characterized by
  a. forming parallel first and second identical data streams,
  b. enhancing said first video stream prior to display, dependent upon whether or not events in said stream are associated with sources of infrared energy that remain stationary with respect to said vessel as said aircraft flies thereover,
  c. feeding said first and second data streams to twin cathode ray tube display units whereby one of said cathode ray display units displays simultaneously said enhanced video signals as a function of time and geometric variables indicative of said set of geographical coordinates while the other cathode ray tube display means displays untreated and unenhanced video signals associated with time and geometric variables also associated with said set of geographical coordinates,
  d. photographing real time images of said twin cathode ray display means to provide a series of comparison thermograms indicative of the temperatures interior of said vessels during regeneration,
  e. communicating said temperature information to ground personnel whereby regeneration conditions associated with said vessel can be changed, as desired, to optimize the regeneration cycle of said vessel.

\* \* \* \* \*